United States Patent [19]
Turner et al.

[11] Patent Number: 6,135,988
[45] Date of Patent: Oct. 24, 2000

[54] ABSORBENT ARTICLE WITH AN ADHESIVE FLAP

[75] Inventors: Laura Jean Turner, Appleton; Chinmay Suresh Betrabet, Neenah; Ruth Ann Lachapell, Menasha, all of Wis.; Thomas Glenn Merrill, Newburgh, Ind.; Barbara Oakley Sauer, Fremont, Wis.

[73] Assignee: Kimberly-Clark Worldwide, Inc., Neenah, Wis.

[21] Appl. No.: 09/215,493

[22] Filed: Dec. 18, 1998

[51] Int. Cl.$^7$ ..................................................... A61F 13/15
[52] U.S. Cl. ........................................... 604/387; 604/386
[58] Field of Search ..................................... 604/387, 378, 604/400, 386, 389, 385.1, 385.2, 385.01, 385.24

[56] References Cited

U.S. PATENT DOCUMENTS

| | | | |
|---|---|---|---|
| 2,512,713 | 6/1950 | Cahill | 128/290 |
| 2,649,858 | 8/1953 | Le Bolt | 128/284 |
| 4,663,220 | 5/1987 | Wisneski et al. | 428/221 |
| 4,850,992 | 7/1989 | Amaral et al. | 604/389 |
| 5,066,289 | 11/1991 | Polski | 604/389 |
| 5,071,415 | 12/1991 | Takemoto | 604/389 |
| 5,226,992 | 7/1993 | Morman | 156/62.4 |
| 5,300,056 | 4/1994 | Webb | 604/389 |
| 5,445,627 | 8/1995 | Mizutani et al. | 604/385.2 |
| 5,593,401 | 1/1997 | Sosalla et al. | 604/385.2 |
| 5,618,281 | 4/1997 | Betrabet et al. | 604/387 |
| 5,658,270 | 8/1997 | Lichstein | 604/387 |
| 5,833,677 | 11/1998 | Sauer | 604/369 |
| 5,836,930 | 11/1998 | Lantz et al. | 604/378 |
| 5,904,675 | 5/1999 | Laux et al. | 604/385.2 |
| 5,938,652 | 8/1999 | Sauer | 604/385.2 |

FOREIGN PATENT DOCUMENTS

| | | |
|---|---|---|
| 0 850 620 A1 | 7/1998 | European Pat. Off. . |
| 0 850 622 A1 | 7/1998 | European Pat. Off. . |
| 0 850 625 A1 | 7/1998 | European Pat. Off. . |
| WO 95/16424 A1 | 6/1995 | WIPO . |
| WO 96/13238 A1 | 5/1996 | WIPO . |
| WO 97/17926 A1 | 5/1997 | WIPO . |
| WO 97/48357 A1 | 12/1997 | WIPO . |
| WO 97/48359 A1 | 12/1997 | WIPO . |
| WO 99/01094 A1 | 1/1999 | WIPO . |

*Primary Examiner*—Sharon Kennedy
*Assistant Examiner*—Cris L. Rodriguez
*Attorney, Agent, or Firm*—Jeffrey B. Curtin

[57] ABSTRACT

An absorbent article with an adhesive flap. The absorbent article has a crotch region, a rear waist region, and a body facing surface positionable adjacent a wearer when the article is in use. The absorbent article includes a backsheet, a liquid permeable topsheet attached to the backsheet, an absorbent structure disposed between said topsheet and said backsheet, and a flap positioned in the rear waist region of the article. The flap has first and second oppositely facing major surfaces wherein the first major surface faces the topsheet and the second major surface forms a portion of the body facing surface of the absorbent article. A substantial portion of the front edge of the flap is a free edge and an adhesive is disposed on the body facing major surface of the flap whereby the adhesive may engage the skin of the wearer when the absorbent article is in use. The adhesive flap thereby prevents the formation of a gap between the absorbent article and the wearer's skin near the rear waist region and, thus, inhibits the leakage of bodily exudates from the absorbent article.

14 Claims, 5 Drawing Sheets

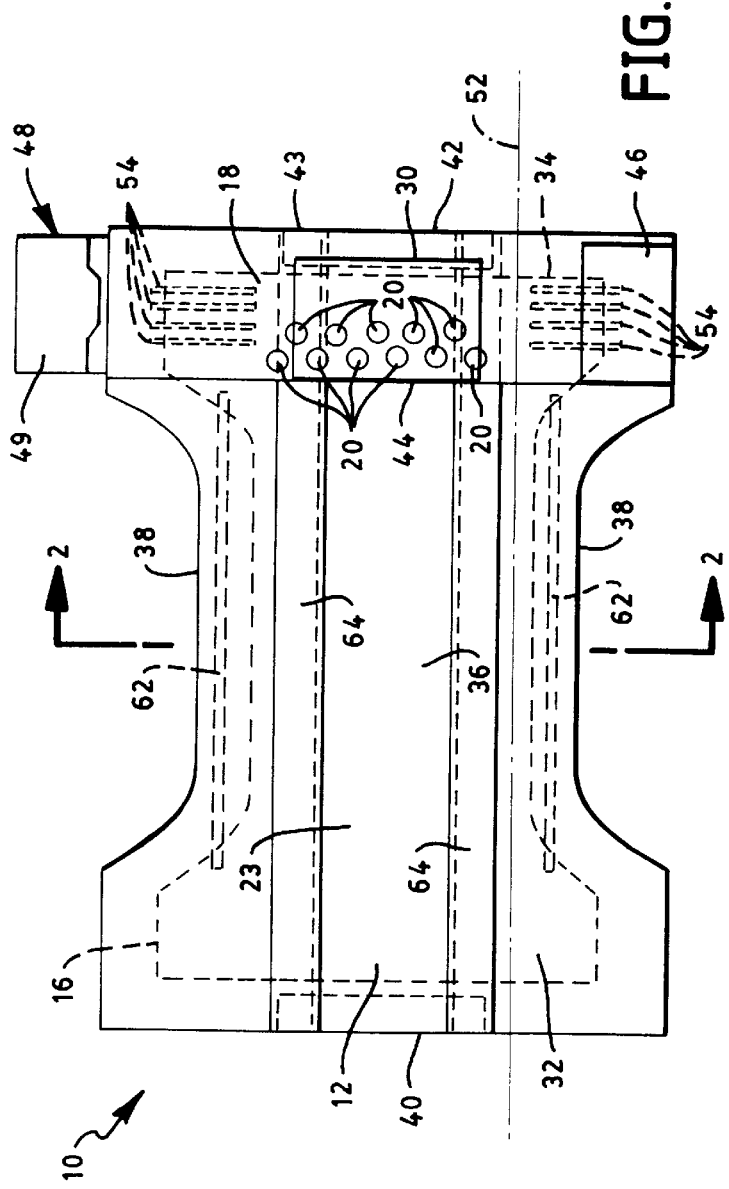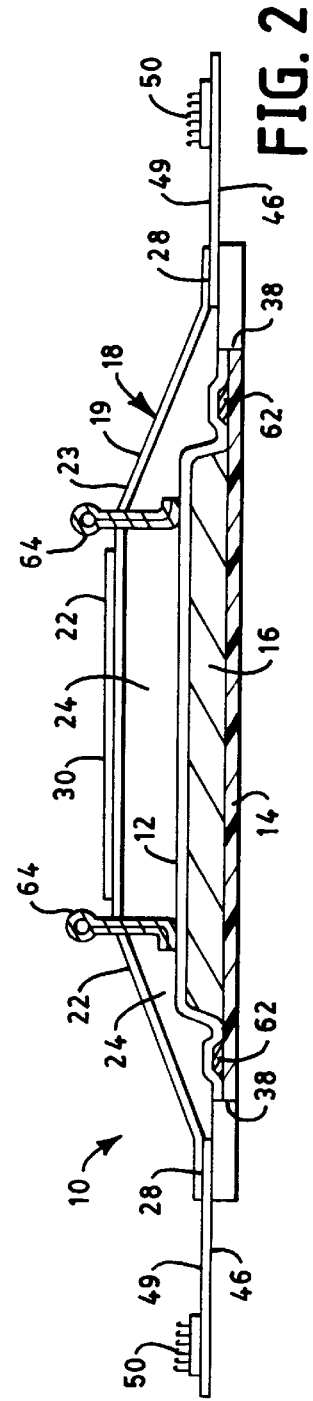

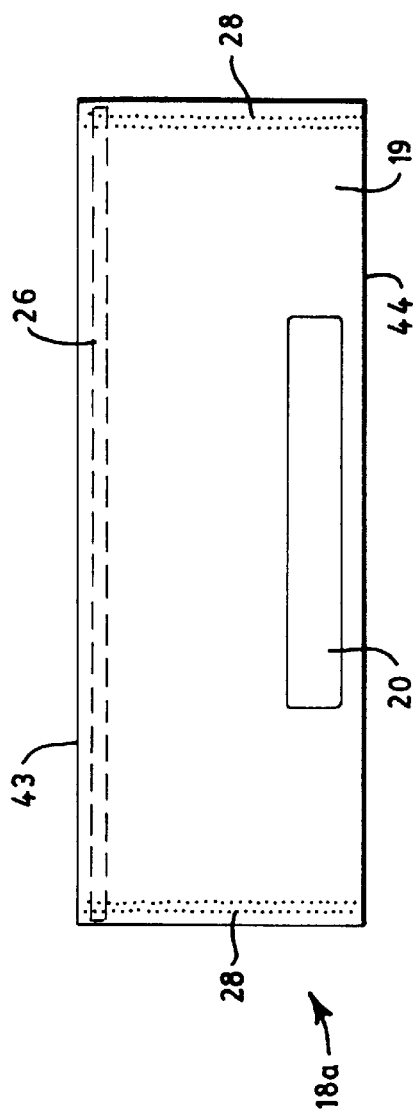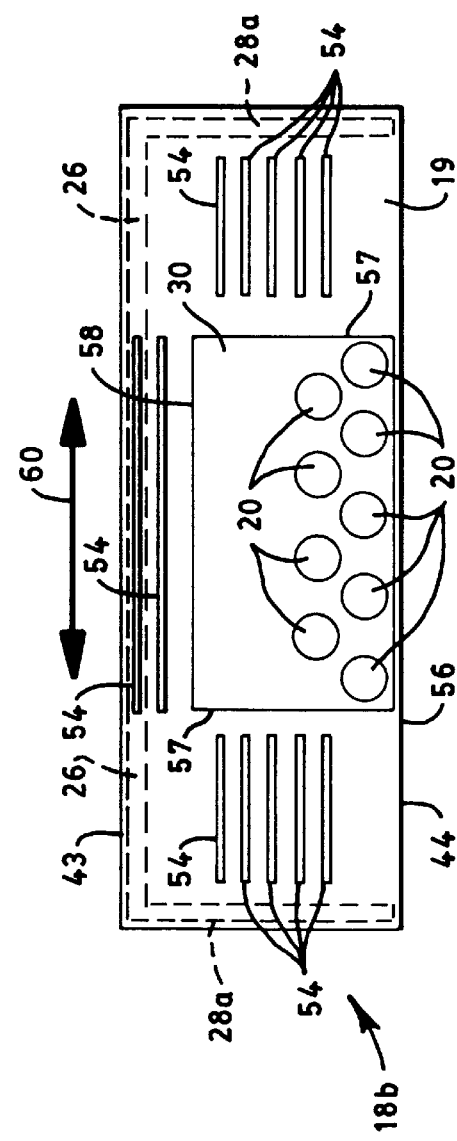

ABSORBENT ARTICLE WITH AN ADHESIVE FLAP

BACKGROUND OF THE INVENTION

1. Field of the Invention

The present invention relates to disposable absorbent articles and, more specifically, to disposable absorbent garments such as diapers, training pants and incontinence garments which are intended to receive and contain fecal insults.

2. Description of the Related Art

Disposable absorbent articles such as diapers, training pants, incontinence garments and similar items are well known to those skilled in the art. Such absorbent articles generally include a front portion, a rear portion and a crotch portion connecting the front portion to the rear portion.

Many conventional absorbent articles, and diapers in particular, are typically secured about the waist of the wearer using fasteners which can be releasably engaged together. Such articles also often include elasticized, longitudinally extending barrier flaps which encircle the upper thighs of the wearer and inhibit the leakage of bodily exudates from between the absorbent article and the legs of the wearer. Such articles have also been known to include rear backflaps which extend laterally in the rear waistband region of the absorbent article. Such backflaps can inhibit the leakage of bodily exudates from the absorbent article along the rear waist band and several different backflap configurations are known in the prior art. In small infants in particular, low viscosity fecal materials may be expelled from the absorbent article via the gluteal groove of the infant resulting in an unpleasant situation for both the wearer and the caregiver. Conventional backflaps are not always sufficient to prevent the expulsion of bodily exudates such as fecal materials along the rear portion of the absorbent article such as those which are expelled along the gluteal groove.

SUMMARY OF THE INVENTION

The present inventors have recognized the difficulties and problems of the prior art and in response thereto have developed an improved absorbent article having a flap which inhibits the leakage of bodily exudates along the rear portion of the absorbent article by utilizing a flap in the rear of the article which is maintained in a leakage inhibiting position by adhering the flap to the skin of the wearer.

In one aspect, the present invention concerns an absorbent article which has a crotch region, a rear waist region, and a body facing surface positionable adjacent a wearer when the article is in use. The absorbent article comprises, i.e., includes but is not limited to, a backsheet, a liquid permeable topsheet attached to the backsheet, an absorbent structure disposed between said topsheet and said backsheet, and a flap positioned in the rear waist region of the article. The flap has first and second oppositely facing major surfaces wherein the first major surface faces the topsheet and the second major surface forms a portion of the body facing surface of the absorbent article. An adhesive is disposed on the second major surface of the flap whereby the adhesive may engage the skin of the wearer when the absorbent article is in use.

Some embodiments of the present invention may include a flap which is attached to the absorbent article along a rear seam which extends in a substantially lateral direction and also has a front edge wherein a substantial portion of the front edge of the flap is a free edge. The flap may be configured whereby the flap has a laterally extending width and the rear seam attaching the flap to the article extends for substantially all of the width of the flap.

Embodiments of the present invention which include a rear seam may also include first and second side seams wherein the side seams extend from a first longitudinal position which is substantially equivalent to the longitudinal position of the rear seam to a second longitudinal position which is substantially equivalent to the longitudinal position of the front edge. The side seams which extend longitudinally forward toward the front edge may also form continuations of the rear seam whereby the sides seams and rear seam form a single continuous seam.

Alternatively, embodiments of the present invention which include a rear seam may have a flap which extends freely between the rear portion of the flap and the front edge, i.e., the flap is not directly attached to the absorbent article between the rear portion of the flap and the front edge, and all of the front edge of the flap is a free edge.

The adhesive disposed on the body facing major surface of the flap may be a polysiloxane adhesive composition and may also include fumed silica. The adhesive may be disposed on the flap in discrete spaced areas or in a single contiguous area. The body facing major surface of the flap may also include an absorbent fibrous material having a fiber orientation direction which is oriented in a substantially lateral direction.

An advantage of the present invention is that the adhesive disposed on the flap secures the flap to the wearer and thereby prevents a gap from forming between the flap and the wearer. Positioning the flap in the rear waist region of the absorbent article allows the flap to be secured to the wearer above the gluteal groove of the wearer where gaps between a non-adhesive flap and the wearer are often formed. Preventing such a gap from forming improves the ability of the flap to prevent the leakage of bodily exudates from the absorbent article. Such a flap is particularly useful for inhibiting the leakage of low viscosity fecal materials which may be forcibly expelled along the gluteal groove of the wearer.

A further advantage of the present invention is that those embodiments which include longitudinally extending side seams may form a pocket between the flap and topsheet for containing fecal materials. Such a pocket lessens the opportunity for fecal materials to contact the skin of the wearer during use, and the skin of the caregiver during the removal and disposal of the article. Thus, those embodiments which have a flap which forms a pocket may provide skin health benefits to the wearer and allow soiled articles to be removed in a relatively clean manner.

An additional advantage of the present invention is that those embodiments which have a flap in which all of the front edge is a free edge and at least the front portion of the flap extends freely, enhance the ability of the flap to remain adhered to the skin of the wearer during use of the article. By providing a freely extending flap, more relative movement between the absorbent article and the portion of the flap adhered to the user is permitted. The flap thereby enhances the ability of the flap to remain adhered to the wearer during use by allowing the absorbent article to shift relative to the wearer by a relatively larger amount before such movement creates tension, and possibly detachment, at the adhesive interface between the flap and wearer's skin.

Yet another advantage of the present invention is provided by the use of an absorbent fibrous material having a fiber orientation direction which is oriented in a substantially lateral direction on the body facing major surface of the flap. Such an absorbent material will tend to wick absorbed fluids in the lateral direction and thereby inhibit the migration of such fluids to the edge of the absorbent article where the absorbed fluids might come into contact with a caregiver or the clothing or bedding of the wearer.

BRIEF DESCRIPTION OF THE DRAWINGS

The invention will be more fully understood and further advantages will become apparent when reference is made to the following detailed description of the invention and the accompanying drawings, in which:

FIG. 1 is a top view of an absorbent article in accordance with the present invention;

FIG. 2 is a cross-sectional view taken through line 2—2 of FIG. 1;

FIG. 4 is a top view of a flap which may be used to form a pocket;

FIG. 5 is a top view of an alternative flap which may be used to form a pocket;

Figure 3:
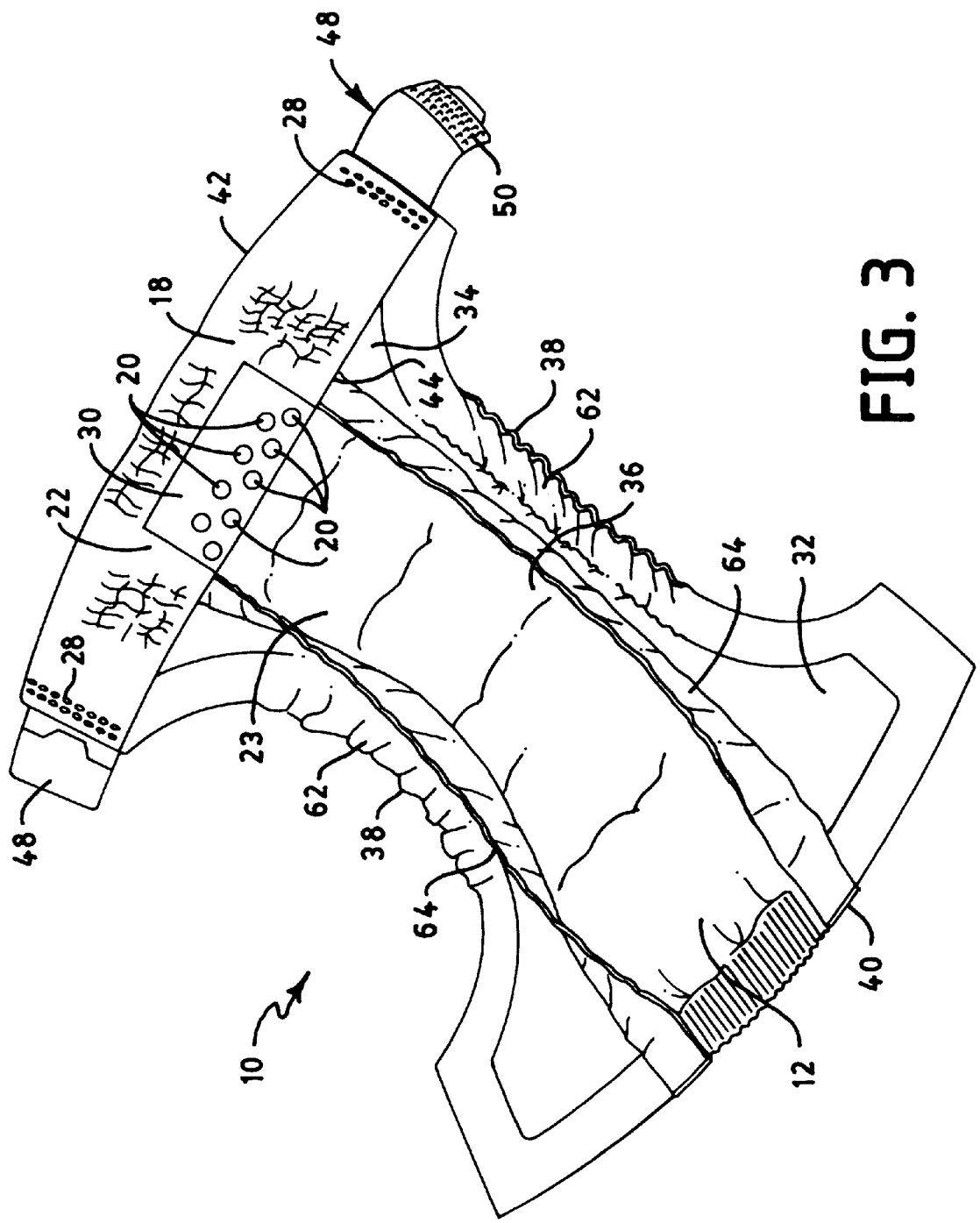
FIG. 3 is a perspective view of the absorbent article of FIG. 1.

Corresponding reference characters indicate corresponding parts throughout the several views. The disclosed embodiments are set forth to illustrate and exemplify the invention. The disclosed embodiments are not intended to be an exhaustive illustration of the invention or to be construed as limiting the scope of the invention to the precise forms disclosed.

DETAILED DESCRIPTION OF THE INVENTION

The following detailed description is made in the context of a disposable diaper which is adapted to be worn by infants about the lower torso. It is readily apparent, however, that the present invention is also applicable for other absorbent articles, such as incontinence garments, training pants, and other similar articles which are used to absorb or contain bodily exudates.

With reference to FIGS. 1–3, an absorbent article in the form of a disposable diaper 10 is illustrated. The disposable diaper 10 has a chassis which includes a liquid permeable topsheet 12, a backsheet 14 and an absorbent structure 16 disposed between the topsheet 12 and the backsheet 14.

The disposable diaper 10 is adapted to be worn about the lower torso and to extend through the crotch of a wearer. The diaper 10 includes a front waist section 32, a rear waist section 34 and an intermediate section 36 which interconnects the front and rear waist sections. As used herein, reference to the front of an absorbent article refers to that portion of the absorbent article which is generally located at the front of the wearer when the article is in use while the rear of the article refers to that portion of the article which is generally located at the rear of the user when in use.

The lateral edges of the intermediate section 36 are defined by a pair of oppositely disposed side edges 38 while the edges of the front 32 and rear 34 waist sections are respectively defined by longitudinally opposed and laterally extending front waist end edge 40 and rear waist end edge 42.

The front 32 and rear 34 waist sections or regions include the general portions of the absorbent article 10 which are constructed to substantially and respectively extend over the wearer's front and rear abdominal regions during use. The intermediate section 36 includes the general portion of the diaper 10 which is constructed to extend through the wearer's crotch region between the legs. The opposed side edges 38 define leg openings and are typically contoured to closely fit the legs of the wearer. The opposed end edges 40, 42 define a waist opening and, in a top view such as FIG. 1, are typically straight but may also be curvilinear.

FIG. 1 is a top plan view of the diaper 10 in a flat, uncontracted state with the surface of the diaper which contacts the wearer, i.e., the bodyside or body facing surface 23, facing the viewer. As can be seen in FIG. 1, the disposable diaper 10 also includes a rear flap 18 which is located in the rear waist region 34 of the diaper 10.

Flap 18 includes two oppositely disposed major surfaces 22, 24. The first major surface 22 faces the body of the wearer during use of the article and forms a portion of the body facing surface 23 of the absorbent article 10 as shown in FIG. 1. The bodyside major surface 22 of the flap 18 includes adhesive areas 20 and may also include an absorbent material 30. The second major surface 24 of the flap 18 faces the topsheet 12 and is shown in FIG. 2.

The flap 18 illustrated in FIGS. 1–3 is attached to the absorbent article 10 along a rear seam and two oppositely disposed side seams. As used herein, the term "seam" does not designate the method of construction used to join two parts together but is used instead to refer to the area or one or more points along which separate parts are joined together. The flap may be attached to the absorbent article by any means known to those skilled in the art such as adhesive bonding, ultrasonic bonding, thermal bonding and the like or with a combination of different means.

In the illustrative embodiment 10, the rear seam extends in a lateral direction near the rear end edge 42 where the flap 18 is adhesively joined to the topsheet 12. The rear seams 26 illustrated FIGS. 4 and 5 are also adhesive seams.

As best seen in FIGS. 3 and 4, side seams 28 may be formed by a plurality of discrete ultrasonic welds. (The flap 18 illustrated in FIGS. 1–3, although not explicitly illustrating the rear seam, is attached in the same manner as the flap 18a illustrated in FIG. 4 which more clearly shows the side seams 28 and rear seam 26.) The two side seams 28 extend from a first longitudinal position which is equivalent to the longitudinal position of the rear seam to a second longitudinal position which is equivalent to the longitudinal position of the front edge 44 of the flap. Although the illustrated seams are rectilinear, alternative configurations may also be used with the present invention.

Although employing a different method of attachment, the illustrated side seams 28 form continuations of the rear seam 26 and extend longitudinally forward toward said front edge 44 of the flaps 18 and 18a. The flap illustrated in FIG. 5, on the other hand, includes side seams 28a which are formed by adhesively bonding the flap 18b to the absorbent article.

The illustrated front edge 44 of flap 18 extends in a substantially lateral direction and is longitudinally spaced from the rear edge 43. Alternative configurations of flap 18 may include curvilinear or inverted "v" shaped front edges which contour the front edge 44 of the flap to the body of the wearer.

A pocket is formed between the flap 18 and the topsheet 12 when a rear seam 26 is combined with two side seams 28. As can be seen in FIG. 2, the front edge 44 of flap 18 forms a free edge between the two side seams 28. In other words, front edge 44 is not directly attached to the diaper 10 over its length extending between the two side seams 28. By allowing front edge 44 to form a free edge between side seams 28, or over a substantial portion of the length of front edge 44, an opening is formed in the pocket defined by flap 18 and topsheet 12.

The front edge 44 is advantageously positioned on the diaper 10 such that front edge 44 is located above the anus of the wearer when the diaper 10 is in use. It is also advantageous to position the front edge 44 of the flap on the diaper 10 so that it will be located above the gluteal groove of the wearer when the diaper 10 is in use. Positioning the pocket opening above the gluteal groove of the wearer allows the pocket formed by the flap 18 and topsheet 12 to be well-positioned to receive and contain fecal materials expelled by the wearer, including those materials which travel upwards along the gluteal groove.

Containing fecal materials in the pocket formed by the flap 18 limits the amount of contact between the fecal materials and the skin of the wearer which can provide skin health benefits to the wearer. Containing fecal materials in the pocket formed by the flap 18 also facilitates the removal of the diaper 10 by reducing the chances of contact between the fecal materials and the skin of either the wearer or the caregiver during the removal process.

Figure 6:
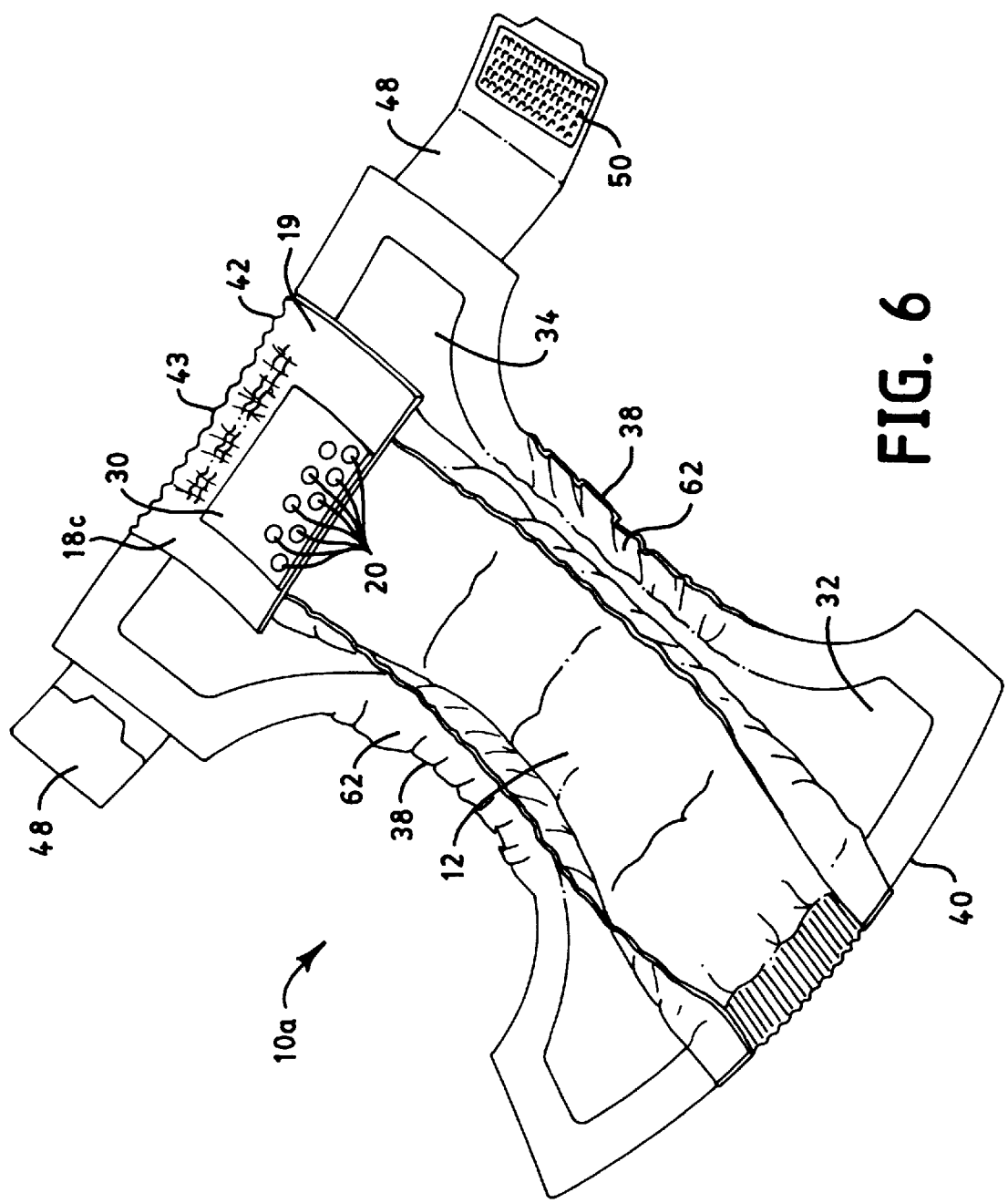
FIG. 6 is a perspective view an alternative absorbent article in accordance with the present invention.

The rear edge 43 of the flap 18 coincides with the rear end edge 42 of the absorbent article in the embodiments illustrated in FIGS. 3 and 6. The rear edge 43 of the flap, however, may also be positioned in an alternative location such as along a line on the bodyside surface 23 spaced longitudinally forward of rear end edge 42.

Figure 7:
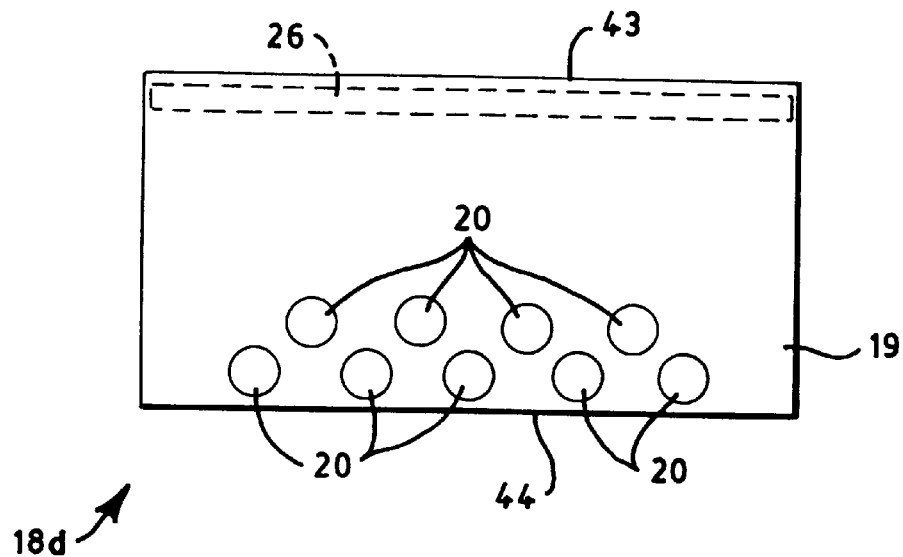
FIG. 7 is a top view of a freely extending flap.
Figure 8:
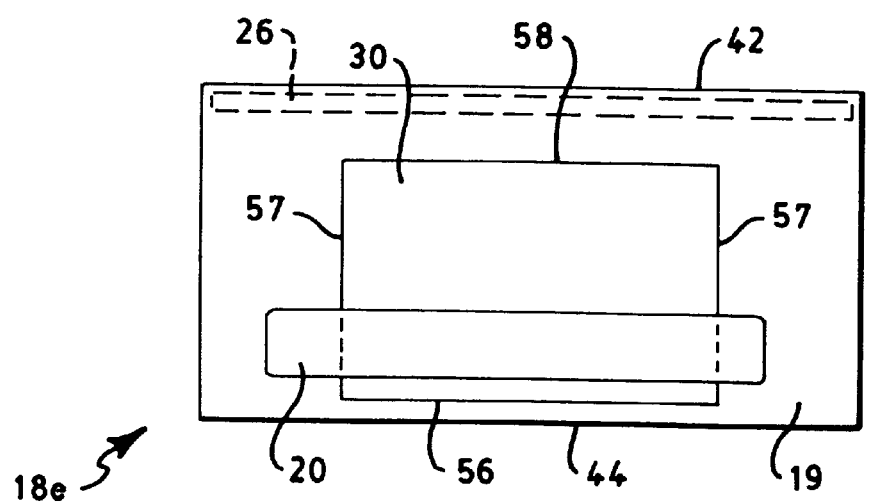
FIG. 8 is a top view of an alternative freely extending flap.

Alternative flaps are also encompassed by the present invention. As illustrated in FIGS. 6–8, flaps may be attached to an absorbent article, such as a diaper, solely along a rear seam 26. In the embodiments of FIGS. 6–8, there are no side seams 28 and the flaps 18c, 18d, and 18e freely extend from the rear seam 26 to the front edge 44 of the flaps. In other words, these flaps are not directly joined to the diaper 10 between the rear seam 26 and the front edge 44 of the flap.

Additional embodiments may include a flap wherein, in addition to rear seam 26, the flap is directly attached by supplemental means, such as partial side seams, in the rear portion of the flap, the entirety of the front edge 44 is a free edge, and the front portion of the flap is freely extending. For example, such a flap could be formed by extending side seams forward from a rear seam 26 for only a portion of the longitudinal expanse of the flap whereby a small pocket is formed in the rear portion of the flap and the front portion of the flap is a freely extending flap. Those having ordinary skill in the art will also recognize that absorbent articles in accordance with the present invention may include flaps which are attached in further alternative configurations in addition to those explicitly disclosed herein to illustrate the present invention.

For the majority of individuals who wear absorbent garments and, in particular, for infants, the small or central portion of the wearer's back is generally concave, i.e., bowed inwards, or flat. As a result it can be difficult to maintain an effective seal between the absorbent article and the wearer at this location. The absorbent articles of the present invention include flaps which are positioned in the rear waist region of the absorbent article whereby the flaps will be generally located in or near this area between the absorbent article and the small of the wearer's back when the article is placed on a wearer.

Adhesive areas 20 which are positioned on the body facing surface 22 of a rear flap are intended to secure the flap to the skin of the wearer. By adhering the flap to the skin of the wearer, the formation of a gap between the absorbent article and the skin of the wearer, through which bodily exudates might escape, is inhibited. For those flaps which form a pocket, the adhesive also facilitates the functioning of the pocket by maintaining the pocket in an open position.

Adhesives which are capable of adequately securing a fabric to skin without causing damage to the skin upon disengagement are suitable for forming the adhesive areas 20. Additionally, the adhesive 20 should not irritate the skin of any appreciable number of wearers.

Suitable adhesives may include hydrogels, silicones, acrylics, polyurethanes, polyesters, and polyamides. Other suitable adhesives include rubber-based adhesives such as those based on styrenebutadiene, polyisobutylene, polybutadiene and polyisoprene; water soluble adhesives such as those based on polyvinyl alcohol, polyvinyl acetate and methyl cellulose; and hot melt adhesives such as those based on block copolymers of styrene-butadiene-styrene, styrene-isoprene-styrene, steyrene-ethylenepropylene-styrene, styrene-ethylenebutylene-styrene, and tetrablock copolymers such as styrene-ethylenepropylene-styrene-ethylenepropylene. Additional suitable adhesives may also include other substances such as tackifying resins, oils and the like.

Advantageously, the adhesive areas 20 of the present invention may be formed using a polysiloxane material. As used herein, a "polysiloxane material" is intended to represent a polymeric material that includes alternate silicon and oxygen atoms with hydrogen or various organic groups attached to the silicon. A detailed description of polysiloxane adhesives is provided in the disclosure of U.S. Pat. No. 5,618,281, issued Apr. 8, 1997 to Betrabet et al., and the disclosure of this patent is incorporated herein by reference.

A pressure sensitive polysiloxane adhesive composition may generally be formed by curing a mixture of a lower alkenyl-functional polysiloxane, such as a vinyl containing polysiloxane, and a hydrogen containing polysiloxane copolymer containing active hydrogen groups. As used herein, the term "active hydrogen groups" is meant to refer to hydrogens which are directly bonded to a silicon atom, such as silicon hydrides and hydrogen containing organopolysiloxanes. The relative amount of each component to be used to prepare the polysiloxane adhesive will be dependent upon such factors as the molar ratio of alkenyl radicals to active hydrogen groups in the uncured composition and the nature of these components, including such variables as polymer chain length, molecular weight, and polymer structure, as well as the adhesive properties desired to be exhibited by the adhesive composition.

Other acceptable methods of inducing crosslinking to prepare the desired polysiloxane adhesive composition include silanol condensation, using organic peroxides, using ultraviolet-initiated crosslinking, using free radical initiated hydrosilation, using high energy radiation crosslinking, or using electron beams.

Starting materials useful in preparing the polysiloxane adhesive composition of the present invention, such as lower alkenyl-functional polysiloxane materials and hydrogen containing polysiloxane copolymer materials containing active hydrogen groups, are well known and may be commercially obtained from such vendors as the Dow Corning Corporation, Wacker Silicones Corporation, and General Electric Corporation.

The components used to prepare the polysiloxane adhesive composition of the present invention can generally be mixed in any manner, such as in bulk or in an organic solvent. The polysiloxane adhesive composition can generally be prepared, with or without the aid of an organic solvent, by simply mixing together the desired components in amounts effective to achieve the desired adhesive properties described herein. The order of mixing the materials together is generally not critical. A suitable method of preparing the polysiloxane adhesive composition is achieved by using a two-part component adhesive formulation, wherein one component comprises a lower alkenyl-functional polysiloxane material and the second component comprises a hydrogen containing polysiloxane copolymer material containing active hydrogen groups.

When materials are mixed together to prepare the polysiloxane adhesive composition, the composition generally begins to cure at a rate which is directly proportional to the temperature of the composition. The polysiloxane adhesive composition may be cured at room temperature or at an elevated temperature by heating the composition. A suitable temperature for curing the polysiloxane adhesive composition is between about 75° C. to about 250° C.

Fumed silica may also be added to the polysiloxane composition to provide an adhesive 20 which is adapted for securing a fabric to the skin of a wearer. For example, a two-part polysiloxane adhesive obtained from the Dow Corning Corporation under the trade designation Sylgard Q3-6636 silicone dielectric gel adhesive parts A and B was mixed with fumed silica obtained from Aldrich Chemical Company to provide a suitable adhesive 20. The adhesive was prepared by mixing 8 grams Dow Corning 6636A with 8 grams Dow Corning 6636B. Fumed silica having an approximate particle size of 0.007 microns was also added to the mixture in the amount of 0.48 grams or less. Polysiloxane adhesives often have an oily feel and the addition of fumed silica can reduce this attribute.

It has been found that caregivers typically remove absorbent articles in two primary methods. In both methods the wearer is positioned on his or her back during removal of the absorbent article. The first method involves lifting the wearer's legs upward and removing the absorbent article in a peeling motion. This first method is typically employed when the wearer has soiled the absorbent article with fecal materials. The second primary method involves sliding the rear of the absorbent article from underneath the wearer. This second method is typically employed when the absorbent article is soiled with urine but has not been soiled with fecal materials.

Although flaps having adhesive areas 20 primarily configured to enhance the ability of the absorbent article to contain fecal materials, absorbent articles which utilize such flaps are often be designed to have the ability to contain and absorb urine insults and may do so in the absence of fecal insults. For such articles, such as disposable diapers, it is advantageous to provide adhesive areas 20 which do not cause undue discomfort when removed from the skin of the wearer in either a peel mode or a shear mode. Suitable adhesives, such as polysiloxane adhesives, used to provide adhesive areas 20 may be removed in either the peel or shear mode without causing undue discomfort to the wearer.

The adhesive areas 20 may be placed on the flaps in either a single contiguous area or in a plurality of discrete, spaced areas. For example, the flaps illustrated in FIGS. 4 and 8 have a single adhesive area 20 while those flaps illustrated in FIGS. 5 and 7 have a plurality of discrete and spaced adhesive areas 20. Although the adhesive areas may be located at alternative locations on the flaps, the adhesive areas 20 are advantageously positioned whereby the adhesive areas 20 are located on the laterally central portion of the flap which is adjacent front edge 44 as shown in the illustrated embodiments.

The use of a freely extending flap enables relative movement to take place between the absorbent article and the user with reduced levels of tension on the adhesive interface and thereby facilitates the continued attachment of the flap. Similarly, the use of a plurality of discrete, spaced areas of adhesive facilitates continued attachment in the presence of relative movement between adjacent portions of the wearer's skin. When a plurality of spaced adhesive areas 20 are utilized, the unadhered areas of the flap separating the adhesive areas may buckle, flex or otherwise compensate for the relative movement of the wearer's skin and areas of adhesive attachment as may take place while the absorbent article is in use. In this manner, the tension created at the adhesive interface between the flap and the wearer's skin may be reduced thereby facilitating the continued attachment of the flap.

The use of a plurality of discrete, spaced areas of adhesive may also promote the breathability of the absorbent article in comparison to the use of a single contiguous adhesive area having the same lateral extent as the plurality of spaced adhesive areas.

The adhesive 20 may be covered, prior to use of the diaper, with a removable cover sheet. The cover sheet can be used to prevent the adhesive from becoming adhered to extraneous surfaces prior to use of the diaper. Suitable materials for use as a cover sheet include silicone coated Kraft papers such as SILOX E1-0 and BL30MG-A SILOX 4P/0 manufactured by Akrosil Corporation.

A release surface 46 may be incorporated into the diaper 10 instead of using a cover sheet. As shown in FIGS. 1–3, diaper 10 may include two fastener tabs 48 having a tab portion 49 and a hook component 50. Fastener tabs 48 are configured to allow hook components 50 to engage a loop component positioned on the front portion of backsheet 14 to secure the diaper 10 about the waist of the wearer. Fastening components such as adhesive tapes, buttons, pins, snaps, mushroom and loop fasteners, and similar devices may alternatively be used to secure the diaper 10 about the waist of the wearer.

In the embodiment illustrated in FIGS. 1–3, however, if a material which is releasably engageable with adhesive areas 20 is used to form the tab portion 49 of the fastener tabs 48, the tab portion 49 may eliminate the need for a cover sheet. For example, by folding the diaper 10 about longitudinally extending fold line 52, as shown in the lower half of FIG. 1, the release surface 46 of the lower fastener tab 48 may be engaged with approximately half of the adhesive areas 20. If the upper tab 48 is similarly positioned and folded, all of the adhesive areas 20 may be engaged with release surfaces 46 prior to packaging and shipment of the diaper 10. When the diaper 10 is subsequently used, the release surfaces 46 will be disengaged from adhesive areas 20 upon unfolding of the diaper 10 and the need for a separable cover sheet can be eliminated. Alternative configurations of diaper 10 and alternative folding patterns can be used to position a non-separable release surface on a different portion of the diaper 10.

Under some circumstances, it may not be desirable to adhere the flap to the skin of the wearer. For example, if the skin of the wearer has been abraded in the area in which the flap would be adhered, adhering the flap to the skin may cause discomfort. For some configurations of the flap, it is possible to position the flap whereby the adhesive will not contact the skin of the wearer when the article is being worn. For example, the flaps illustrated in FIGS. 6–8 may be folded backwards over rear end edge 42 to attach the adhesive 20 to the backsheet 14, or doubled over to attach the adhesive 20 to the rear portion of the flap on either major surface of the flap, to thereby allow the diaper 10 to be used without adhering the flap to the skin of the wearer.

The material layer 19 used to form the flap may be either liquid permeable or liquid impermeable. It is generally preferred that the flap layer 19 be formed from a material which is substantially impermeable to liquids. Layer 19 may be formed from a single unitary layer of material or by a laminate material comprising several individual layers. For example, the flap may be formed from a material layer 19 manufactured from a thin plastic film or other flexible liquid-impermeable material such as a polyethylene film having a thickness of from about 0.013 millimeter (0.5 mil) to about 0.051 millimeter (2.0 mils).

If it is desired to present a more clothlike feeling, the layer 19 may comprise a polyethylene film having a nonwoven web laminated to the body facing surface 22, such as a spunbond web of polyolefin fibers. For example, a polyethylene film having a thickness of about 0.015 millimeter (0.6 mil) may be thermally laminated to a spunbond web of polyolefin fibers, with the fibers having a thickness of about 1.5 to 2.5 denier per filament and the nonwoven web produced thereby having a basis weight of about 24 grams per square meter (0.7 ounce per square yard). Methods of forming such clothlike layers are known to those skilled in the art.

Further, the flap layer 19 may be formed of a woven or nonwoven fibrous web layer which has been totally or partially constructed or treated to impart a desired level of liquid impermeability. Still further, the flap layer 19 may optionally be composed of a micro-porous "breathable" material which permits vapors to pass through the flap while still preventing liquid exudates from passing through the flap. The backsheet 14 may be formed using the same materials as those used for the flap layer 19.

Flap layer 19 may also include a layer of elastomeric material. For example, the layer 19 may be formed by or include a stretch-bonded-laminate (SBL) material, a neck-bonded-laminate (NBL) material, an elastomeric film, an elastomeric foam, or similar elastomeric material. Such materials are known in the art. For example, meltblown elastomeric fibrous webs are described in U.S. Pat. No. 4,663,220, issued May 5, 1987 to T. Wisneski et al., the disclosure of which is hereby incorporated by reference and examples of NBL materials are described in U.S. Pat. No. 5,226,992 issued Jul. 13, 1993 to Mormon, the disclosure of which is also hereby incorporated by reference.

A non-elastomeric flap may also be modified to render portions of the flap elastically contractable to contour the flap to the wearer's body. As illustrated in FIGS. 1 and 5, different portions of the flap may include elastic strands which are laterally elongated and adhesively attached to the flap. Suitable elastic strands are known to those skilled in the art. For example, a suitable elastic strand may be composed of a 470 decitex Lycra elastomer or a 620 decitex Lycra elastomer, which are obtainable from E.I. DuPont de Nemours Co., or similar elastomers. Alternatively, a piece of elastomeric material, e.g., an SBL, NBL or elastomeric film or foam, may be adhesively attached to selected portions of the flap in an elongated condition to provide the desired elasticity.

The flap may also include an absorbent material 30 located on the body facing surface 22 of the flap. Absorbent material 30 provides a means for absorbing and containing small quantities of waste materials which may be present at the body facing surface of the flap. Adhesive areas 20 are configured to prevent escape of bodily exudates, however, it may still be possible for minor quantities of fecal fluids and particulates to occasionally migrate between the flap and the wearer's skin. Thus, although the absorbent material 30 has only a small absorbent capacity in comparison to the absorbent structure 16, the functioning of the flap should prevent any significant quantities of waste fluids from reaching the area between the flap and the wearer's skin.

Fecal fluids may produce noticeable staining, even when present in only minor quantities, if absorbed by the clothing of the wearer or caregiver. Furthermore, it is undesirable for skin health and cleanliness reasons for such fluids to contact the skin of the wearer or caregiver. Thus, the provision of an absorbent material 30 with only a small total absorbent capacity provides a valuable function. By utilizing a fibrous material to form the absorbent material 30, the absorbent material will include void spaces between the fibers which may retain small quantities of fecal particulate matter in addition to fluids.

The absorbent material 30 may cover all or part of the body facing surface 22 of the flap. As illustrated in FIGS. 5 and 8, the absorbent material 30 may be advantageously positioned laterally central and longitudinally forward on the flap. The front edge 56 of absorbent material 30 may be positioned near the front edge 44 of the flap and is advantageously spaced at least about 0.5 cm rearwardly of the flap front edge 44. The side edges 57 of absorbent material 30 extend rearwardly to the rear edge 58 of the absorbent material 30. The rear waist end edge 42 may come into contact with the clothing or bedding materials of the wearer and it is desirable for this edge to not include an exposed layer of absorbent material which could become saturated with waste fluids. Thus, the rear edge 58 is advantageously spaced forward of rear end edge 42. The rear edge 58 may be advantageously spaced at least about 1.5 cm forward of the rear end edge 42, however, alternative spacings may also be employed.

The basis weight of the absorbent material 30 may be varied and suitable basis weights include at least about 30 grams per square meter, at least about 50 grams per square meter, and at least about 75 grams per square meter. The absorbent material 30 may be joined to the flap in a variety of manners such as by heat sealing, sonic bonding, adhesives and other attachment methods known in the art.

A number of different materials may be used to form absorbent material 30. For example, the absorbent material 30 can include a nonwoven material such as a spunbond, meltblown, spun laced or carded web of natural fibers, synthetic fibers, polymeric fibers, similar fibrous materials, or combinations thereof. Alternatively, the absorbent material 30 may include a foam material or an uncreped through air dried material comprising cellulosic fibers.

Desirably, the absorbent material 30 includes hydrophilic fibers such as cellulose or rayon fibers. Nonwoven materials formed from hydrophobic materials, however, may be treated with a surfactant to render them generally hydrophilic and such treated materials may also be used to form an effective absorbent material 30.

The fibers may also be oriented in one direction such that the absorbent material 30 has improved fluid wicking in that direction. For example, the absorbent material 30 illustrated in FIG. 5 contains fibers which are oriented in the lateral direction 60. By providing an absorbent material having a fiber orientation direction which is in a lateral direction, the absorbent material 30 will tend to wick absorbed fluids in a lateral, rather than longitudinal, direction. Thus, the absorbed liquids will not have a tendency to migrate towards the rear waist end edge 42 where an exposed edge of a saturated or wetted layer of material might come into contact with the clothing or bedding of the wearer or the skin or clothing of a caregiver.

In a specific embodiment, the absorbent material 30 may be formed from a nonwoven material such as a bonded carded web which includes natural fibers. One such material is a bonded carded web commercially available from E. I. DuPont de Nemours Co. a business having offices located in Delaware under the trade designation SONTARA 8423. Such material includes about 70 weight percent rayon fibers and about 30 weight percent polyester fibers and has a basis weight of about 78 grams per square meter.

When there is an absorbent material 30 present on the flap, the adhesive areas 20 may be advantageously disposed on that portion of the body facing surface 22 of the flap which is defined by the absorbent material 30. When adhesive areas 20 are placed on the absorbent material 30, all of the adhesive areas 20 may be located on the absorbent material 30, as exemplified by the embodiment illustrated in FIG. 5, or, as exemplified by the embodiment illustrated in FIG. 8, the adhesive area 20 may extend beyond the limits of the absorbent material 30.

Alternative embodiments may employ absorbent material 30 as a carrier material wherein the adhesive is applied to the absorbent material 30 whereby the adhesive areas 20 are formed by that portion of the applied adhesive which has bled-through the absorbent material 30. Such a carrier material may be a spunbond material and may not necessarily perform an absorbent function.

The topsheet 12 of the diaper 10 is a conventional liner and suitably presents a body facing surface which is compliant, soft feeling, and nonirritating to the wearer's skin. The topsheet 12 may be advantageously employed to help isolate the wearer's skin from liquids held in the absorbent structure 16. For example, the topsheet may be less hydrophilic than the absorbent structure 16 to present a relatively dry surface to the wearer while remaining sufficiently porous to be liquid permeable, permitting liquid to readily penetrate through its thickness.

Suitable topsheet materials are well known in the art and include a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. One nonwoven fabric well-suited for use as topsheet 12 is a spunbond, polypropylene fabric composed of about 2.8–3.2 denier fibers formed into a web having a basis weight of about 22 grams per square meter and a density of about 0.06 gram per cubic centimeter and which has been surface treated with a surfactant.

Absorbent materials suited for use as absorbent structure 16 are also well known in the art. The absorbent structure 16 may comprise a matrix of hydrophilic fibers, such as a web of cellulosic fluff, mixed with particles of a high-absorbency material commonly known as superabsorbent material. In a particular embodiment, the absorbent structure 16 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. Alternatively, the absorbent structure 16 may comprise a laminate of fibrous webs and superabsorbent material or other suitable means of maintaining a superabsorbent material in a localized area.

Suitable high-absorbency materials are well known in the art and may include natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

The absorbent structure 16 may have any of a number of shapes. For example, the absorbent structure may be rectangular, I-shaped, or T-shaped. It is generally preferred that the absorbent structure 16 be narrower in the intermediate section 36 than in the front 32 or rear 34 waist sections.

The absorbent structure may also include a surge layer to rapidly distribute liquids throughout the absorbent structure 16 and prevent the pooling of liquids on the topsheet 12. Such surge layers are well known in the art and are often disposed immediately below the bodyside liner.

The topsheet 12 and backsheet 14 may be attached together so as to form a pocket in which the absorbent structure 16 is located. The topsheet 12 and backsheet 14 may be so attached by either directly joining the topsheet 12 and backsheet 14 together or by attaching the topsheet 12 and backsheet 14 together via one or more intermediate components of the absorbent article. The side edges and longitudinal end edges of the disposable diaper 10 may be suitably formed by portions of the topsheet 12 and backsheet 14 which extend beyond the sides and longitudinal ends of the absorbent structure 16. The different components of the disposable diaper 10 may be bonded together by any means known to those skilled in the art such as adhesive bonding, ultrasonic bonding, thermal bonding and the like.

The diaper 10 may also include a pair of elasticized, longitudinally-extending leg cuffs 62. The leg cuffs 62 are generally adapted to fit about the legs of the wearer in use and serve as a mechanical barrier to the lateral flow of body exudates. The diaper 10 may also include a front and rear waist elastic to secure the diaper about the front and back waist of the wearer when in use. The leg cuffs 62 and waist elastics may be elasticized by elastic members as are well known to those skilled in the art. The diaper 10 may also include a pair of elasticized, longitudinally-extending containment flaps 64 which are configured to maintain an upright, perpendicular arrangement in at least the intermediate section 36 of the diaper 10 to serve as an additional barrier to the lateral flow of body exudates.

While this invention has been described in detail, it will be readily apparent to a person of ordinary skill in the art that various changes and modifications can be made without departing from the spirit and general principles of the invention. All of such changes and modifications are contemplated as being within the scope of the present invention as defined by the subjoined claims. Furthermore, this application is intended to cover such departures from the present disclosure as come within known or customary practice in the art.

What is claimed is:

1. An absorbent article having a crotch region, a rear waist region, and a body facing surface positionable adjacent a wearer when said article is in use, said article comprising:
   a backsheet;
   a liquid permeable topsheet attached to said backsheet;
   an absorbent structure disposed between said topsheet and said backsheet;
   a flap positioned in the rear waist region of said article and having first and second oppositely facing major surfaces, said first major surface facing said topsheet, said second major surface forming a portion of the body facing surface of said article wherein said flap is attached to said article along a rear seam which extends in a substantially lateral direction, said flap further comprising a front edge which extends in a substantially lateral direction and is longitudinally spaced from said rear seam and wherein said flap freely extends between said front edge and a rear portion of said flap and wherein all of said front edge is a free edge; and
   an adhesive disposed on said second major surface whereby said adhesive is engageable with the skin of the wearer when said article is in use.

2. An absorbent article according to claim 1, said flat further comprising first and second side seams, said side seams extending from a first longitudinal position substantially equivalent to a longitudinal position of said rear seam to a second longitudinal position between said rear seam and said front edge.

3. An absorbent article according to claim 1 wherein said flap freely extends between said rear seam and said front edge.

4. An absorbent article according to claim 1 wherein said flap includes a liquid impermeable layer.

5. An absorbent article according to claim 1 wherein said flap includes an absorbent material disposed on said second major surface.

6. An absorbent article according to claim 5 wherein said absorbent material is a fibrous material having a fiber orientation direction which is disposed in a substantially lateral direction.

7. An absorbent article according to claim 6 wherein said absorbent material has a rear edge which is spaced forwardly of a rear, laterally extending, end edge of said absorbent article.

8. An absorbent article according to claim 1 wherein said adhesive is disposed in a plurality of discrete, spaced adhesive areas.

9. An absorbent article according to claim 1 wherein said adhesive comprises a polysiloxane adhesive composition.

10. An absorbent article according to claim 9 wherein said adhesive further comprises fumed silica.

11. An absorbent article according to claim 1 wherein said adhesive is centrally disposed on a portion of said second major surface near a front edge of said flap.

12. An absorbent article having a crotch region, a rear waist region, and a body facing surface positionable adjacent a wearer when said article is in use, said article comprising:
    a backsheet;
    a liquid permeable topsheet;
    an absorbent structure disposed between said topsheet and said backsheet;
    a flap positioned in the rear waist region of said article and having first and second oppositely facing major surfaces, said first major surface facing said topsheet layer, said second major surface forming a portion of the body facing surface of said article, said flap having a laterally extending width and being attached to said article along a rear seam which extends for substantially all of said width and said flap having first and second side seams, said side seams forming continuations of said rear seam and extending longitudinally forward to a front edge of said flap; and
    an adhesive disposed on said second major surface whereby said adhesive is engageable with the skin of the wearer when said article is in use.

13. An absorbent article according to claim 12 wherein said flap freely extends between said front edge and a rear portion of said flap and wherein all of said front edge is a free edge.

14. An absorbent article according to claim 12 wherein all of said front edge is a free edge and said flap freely extends between said rear seam and said front edge.

* * * * *